United States Patent [19]
Ogawa et al.

[11] Patent Number: 5,658,578
[45] Date of Patent: Aug. 19, 1997

[54] COSMETIC COMPOSITION

[75] Inventors: Haruo Ogawa; Shoji Nishiyama; Kenzo Ito, all of Kanagawa, Japan

[73] Assignee: Shiseido Company, Ltd., Tokyo, Japan

[21] Appl. No.: 505,666

[22] Filed: Jul. 21, 1995

[30] Foreign Application Priority Data

Jun. 1, 1995 [JP] Japan .................................. 7-158448

[51] Int. Cl.$^6$ .................................................. A61K 7/48
[52] U.S. Cl. ........................ 424/401; 514/844; 514/847; 514/944
[58] Field of Search ........................ 424/401; 514/844, 514/847, 944

[56] References Cited

FOREIGN PATENT DOCUMENTS

| | | |
|---|---|---|
| 0 473 502 | 3/1992 | European Pat. Off. . |
| 1440795 | 4/1966 | France . |
| 43 23 615 | 1/1995 | Germany . |
| 3-7212 | 1/1991 | Japan . |
| 3-279316 | 12/1991 | Japan . |
| 7-76513 | 3/1995 | Japan . |

OTHER PUBLICATIONS

DATABASE WPI, Week 7203, Derwent Publications Ltd., London, GB; AN 72–04883T & JP–B–47 001 479 (Daiichi Seiyaku Co Ltd).

*Primary Examiner*—Jyothsna Venkat
*Attorney, Agent, or Firm*—Cushman Darby & Cushman Intellectual Property Group of Pillsbury Madison & Sutro, LLP

[57] ABSTRACT

A preparation for external application to the skin which comprises disodium adenosine triphosphate and tranexamic acid for prevention of skin roughening and skin improvement. The preparation further contains ginseng extract.

4 Claims, No Drawings

COSMETIC COMPOSITION

FIELD OF THE INVENTION

This invention relates to preparations for external application to the skin, more particularly external preparations having powerful effects of preventing skin roughening and improving the skin. The external preparation of the present invention is suitably applied to cosmetics, such as clear lotions, creams, milky lotions, facial packs, and scalp care cosmetics, or medicines, such as ointments for wounds or inflammation.

BACKGROUND OF THE INVENTION

One of the major purposes of external preparations for the skin such as cosmetics consists in prevention of skin roughening and skin improvement. For this purpose, humectants, such as glycerin, polyethylene glycol, sorbitol, mucopolysaccharides, and hyaluronic acid, have been incorporated into skin care preparations. However, these substances are not sufficiently effective in prevention of surface roughening and improvement of the skin, and more effective substances have been demanded.

Tranexamic acid, on the other hand, is known effective on the skin in healing of wounds, prevention of skin roughening and skin improvement and has been added to medicines and cosmetics (see JP-B-47-1479, the term "JP-B" as used herein means an "examined published Japanese patent application"). However, preparations for external application containing a large amount of tranexamic acid are sticky and feel unpleasant when applied to the skin. Further, ginseng extract is known to be a Chinese medicine having blood flow accelerating action. It has recently been reported that combination of ginseng extract with γ-amino-β-hydroxybutyric acid provides fast-acting cosmetics for anti-aging (see JP-A-7-76513, the term "JP-A" as used herein means "an unexamined published Japanese patent application").

SUMMARY OF THE INVENTION

The present invention has been completed by taking these circumstances into consideration. An object of the present invention is to provide a preparation for external application to the skin which produces improved effects on the skin in healing of wounds, prevention of skin roughening, and skin improvement.

The present invention relates to a preparation for external application to the skin which contains disodium adenosine triphosphate and tranexamic acid.

In a preferred embodiment of the present invention, the preparation further contains ginseng extract.

DETAILED DESCRIPTION OF THE INVENTION

Disodium adenosine triphosphate is preferably used in an amount of 0.0005 to 3.0% by weight, still preferably 0.0005 to 0.3% by weight, based on the total preparation. At a disodium adenosine triphosphate content of 0.0005% or more, an increased skin improving effect can be obtained, and the feeling of use, such as skin tension. If the disodium adenosine triphosphate content exceeds 3.0%, the preparation tends to have deteriorated feeling of use, for example, tends to become sticky.

Tranexamic acid is preferably used in an amount of 0.01 to 3.0% by weight, still preferably 0.1 to 3.0% by weight. At a tranexamic acid content of 0.01% or more, an increased effect on growth of skin cells and an improved feeling of use, such as moistness, can be obtained. If the tranexamic acid content exceeds 3.0%, the preparation tends to have deteriorated feeling of use, for example, tends to become sticky.

Ginseng extract, if added to the preparation, is preferably used in an amount of 0.005 to 10.0% by weight, still preferably 0.01 to 10.0% by weight. At a ginseng extract content of 0.005% or more, an increased improving effect on the skin can be obtained. If the content exceeds 10.0%, the preparation tends to feel sticky.

"Ginseng extract" as referred to herein is an extract of Panax ginseng C. A. Meyer (Araliaceae), prepared by evaporating an ethanol extract of the plant to dryness and re-dissolving the solid in ethanol in a concentration of 50% by weight. Ginseng extract is highly valued as a Chinese medicine having actions such as acceleration of blood flow of the skin and entered in Japanese Pharmacopeia.

The preparations according to the present invention denote those externally applied to the skin, such as cosmetics, pharmaceuticals, and non-medical applications and may therefore take a wide variety of forms, such as clear solutions, microemulsions, emulsions, powders, oily liquids, gels, ointments, water-oil two phase systems, water-oil-powder three phase systems, and the like.

If desired, the preparations may contain other components generally used in cosmetics or pharmaceuticals as long as the effects of the present invention are not impaired.

Such other components include powdery components, e.g., titanium dioxide, mica, and talc; oils, e.g., avocado oil, corn oil, olive oil, rapeseed ol, evening primrose oil, castor oil, sunflower oil, tea seed oil, rice bran oil, jojoba oil, cacao oil, palm oil, squalane, squalene, beef tallow, Japan wax, molasses, candelilla wax, carnauba wax, whale wax, lanolin, silicone oil, fluorine oil, liquid paraffin, ceresin, vaseline, polyoxyethylene (POE) (8 mol) oleyl alcohol ether, and glycerol monooleate; higher alcohols e.g., capryl alcohol, lauryl alcohol, myristyl alcohol, and cetyl alcohol; sterols, e.g., cholesterol and phytosterol; higher fatty acids, e.g., capric acid, lauric acid, myristic acid, palmitic acid, stearic acid, behenic acid, lanolin fatty acids, linoleic acid, and linolenic acid; ultraviolet absorbers, e.g., p-aminobenzoic acid, homomenthyl-7N-acetylanthranilate, butylmethoxybenzoylmethane, glycerol mono-2-ethylhexanoate di-p-methoxycinnamate, amyl salicylate, octyl cinnamate, and 2,4-dihydroxybenzophenone; moisturizers, e.g., polyethylene glycol, glycerin, sorbitol, xylitol, and maltitol; thickeners, e.g., methyl cellulose, ethyl cellulose, gum arabic, carboxyvinyl polymer, alkyl-modified carboxyvinyl polymers, polyvinyl alcohol, montmorillonite, and Laponite (synthetic Hectorite); organic solvents, e.g., ethanol and 1,3-butylene glycol; antioxidants, e.g., butylhydroxytoluene, tocopherol, and phytic acid; antimicrobial antiseptics, e.g., benzoic acid, salicylic acid, sorbic acid, alkyl p-hydroxybenzoates (e.g., ethyl p-hydroxybenzoate or butyl p-hydroxybenzoate), and hexachlorophene; amino acids, e.g., glycine, alanine, valine, leucine, serine, threonine, phenylalanine, tyrosine, aspartic acid, asparagine, glutamine, taurine, arginine, and histigine, and alkali metal salts and a hydrochloride of these amines; organic acids, e.g., acylsarcosine (e.g., sodium lauroylmethylsarcosine), glutathione, malic acid and tartaric acid; vitamins such as vitamin A and its derivatives, vitamin B group and its derivatives including vitamin B6 hydrochloride, vitamin B6 tripalmitate, vitamin B6 dioctanoate, vitamin B2 and its derivatives, vitamin B12, and vitamin B15 and its derivatives; vitamin C and its derivatives, e.g., ascorbic acid, ascorbic acid sulfate (salts), ascorbic acid phosphate (salts), and ascorbic acid dipalmitate; vitamin E and its derivatives such as α-, β-, and γ-tocopherol, vitamin E acetate and vitamin E nicotinate; vitamin D group, vitamin H, pantothenic acid, and pantethine; drugs, e.g., nicotinamide, benzyl nicotinate, γ-oryzanol, allantoin, glycyrrhizinic acid (salts), glycyrrhetinic acid and its derivatives, hinokitiol, Mucidin, bisabolol, eucalyptol, thymol, inositol, saponins (e.g., saikosaponin, dishcloth gourd saponin, and soapberry saponin), pentothenyl ethyl ether, ethynylestradiol, cepharanthine, placenta extract, and arbutin; natural extract of plants, such as yangti (*Rumex japonicus* Houtt.), kushen (*Sophora flavescens* Air.), candock, orange, sage, manifoil, common mallow, chuanxiong (*Cnidii officinale* Makino), Japanese green gentian (*Swertia japonica* Makino), thyme, danguii (*Angelica sinensis* (Oliv.) Diels), orange peel, birch, field horsetail, dishcloth gourd, hourse chestnut tree, creeping saxifrage (*Saxifrage stolonifera*), arnica, lily, mugwort, peony, aloe, gardenia, etc., obtained by using an organic solvent, e.g., alcohols, polyhydric alcohols, water, and aqueous alcohols; dyestuffs; nonionic surface active agents, e.g., sorbitan monolaurate, sorbitan monopalmitate, sorbitan sesquioleate, sorbitan trioleate, polyoxyethylene sorbitan monoluaurate, polyoxyethylene sorbitan monostearate, polyethylene glycol monooleate, polyoxyethylene alkyl ethers, polyglycol diethers, lauroyl diethanolamide, fatty acid isopropanolamide, maltitol hydroxyfatty acid ethers, alkylated polysaccharides, alkyl glucosides, and sugar esters; cationic surface active agents, e.g., stearyltrimethylammonium chloride, benzarkonium chloride, and laurylamine oxide; anionic surface active agents, e.g., sodium palmitate, sodium laurate, sodium laurylsulfate, potassium laurylsulfate, alkylsulfate triethanolamine ethers, Turkey red oil, linear dodecylbenzenesulfate, polyoxyethylene hardened castor oil maleic acid, and acylmethyltaurine; amophoteric surface active agents, flavors, purified water, and the like.

The present invention will now be illustrated in greater detail with reference to Examples, but it should be understood that the present invention is not construed as being limited thereto. Unless otherwise indicated, all the percetns are by weight.

EXAMPLES 1 TO 5 AND COMPARATIVE EXAMPLES 1 TO 6

Preparations for external application to the skin were prepared according to the formulation shown in Tables 1 and 2 and tested for an improving effect on rough skin and for stickiness according to the following test methods. The results obtained are shown in the respective table.

1) Test of Effect on Rough Skin:

The skin on the back of a healthy man was treated with a 3% aqueous solution of sodium dodecylsulfate to induce skin toughening. Two hours later, 20 µl of the preparation was applied thereto once a day for consecutive 5 days. On the 6th day, the condition of the skin was observed by naked eyes and scored according to the following standards. The higher the score, the higher the improving effect on skin roughness.

Standards of Score:
1. Drying of the corneum over a wide area, peeling, and severe erythema were observed.
2. Drying of the corneum, peeling, and moderate erythema were observed.
3. Drying of the corneum was observed, but no peeling. Slight erythema was observed.
4. Neither drying of the corneum nor peeling was observed. Slight erythema was observed.
5. None of drying of the corneum, peeling and erythema was observed.

The test was carried out on 10 men for each preparation, and the improving effect on rough skin was evaluated based on the average score according to the following rating standards.

Rating Standards:
A. Average score not lower than 4.
B. Average score not lower than 3 and lower than 4.
C. Average score not lower than 2 and lower than 3.
D. Average score lower than 2.

2) Test of Stickiness:

The degree of stickiness was evaluated on the skin of the same 10 men based on the following standards of score and rating standards.

Standards of Score:
1. Non-sticky
2. Less sticky
3. Neither sticky nor non-sticky
4. Slightly sticky
5. Sticky Rating Standards:
A. Average score not lower than 4.
B. Average score not lower than 3 and lower than 4.
C. Average score not lower than 2 and lower than 3.
D. Average score lower than 2.

TABLE 1

| Formulation | Example No. | | | | |
|---|---|---|---|---|---|
| | 1 | 2 | 3 | 4 | 5 |
| Tranexamic acid | 2.0 | 0.1 | 5.0 | 0.05 | 2.0 |
| Disodium adenosine triphophate | 0.1 | 0.001 | 0.001 | 0.001 | 0.1 |
| Ginseng extract | 1.0 | 0.01 | 0.01 | 0.01 | — |
| Propylene glycol | 1.0 | 1.0 | 1.0 | 1.0 | 1.0 |
| Citric acid | 0.04 | 0.04 | 0.04 | 0.04 | 0.04 |
| Sodium citrate | 0.16 | 0.16 | 0.16 | 0.16 | 0.16 |
| Ethanol | 10.0 | 10.0 | 10.0 | 10.0 | 10.0 |
| POE (20) lauryl ether | 0.5 | 0.5 | 0.5 | 0.5 | 0.5 |
| Methyl p-hydroxy-benzoate | 0.1 | 0.1 | 0.1 | 0.1 | 0.1 |
| Flavor | proper amount | proper amount | proper amount | proper amount | proper amount |
| Purified water | balance | balance | balance | balance | balance |
| Improving effect on rough skin | A | A | A | B | B |
| Stickiness | B | A | C | A | B |

TABLE 2

| Formulation | Comparative Example No. | | | | | |
|---|---|---|---|---|---|---|
| | 1 | 2 | 3 | 4 | 5 | 6 |
| Tranexamic acid | 2.0 | 2.0 | — | — | — | — |
| Disodium adenosine triphophate | — | — | 0.1 | 0.1 | — | — |
| Ginseng extract | 1.0 | — | 1.0 | — | 1.0 | — |
| Propylene | 1.0 | 1.0 | 1.0 | 1.0 | 1.0 | 1.0 |

TABLE 2-continued

| | Formulation Comparative Example No. | | | | | |
|---|---|---|---|---|---|---|
| | 1 | 2 | 3 | 4 | 5 | 6 |
| glycol | | | | | | |
| Citric acid | 0.04 | 0.04 | 0.04 | 0.04 | 0.04 | 0.04 |
| Sodium citrate | 0.16 | 0.16 | 0.16 | 0.16 | 0.16 | 0.16 |
| Ethanol | 10.0 | 10.0 | 10.0 | 10.0 | 10.0 | 10.0 |
| POE (20) lauryl ether | 0.5 | 0.5 | 0.5 | 0.5 | 0.5 | 0.5 |
| Methyl p-hydroxybenzoate | 0.1 | 0.1 | 0.1 | 0.1 | 0.1 | 0.1 |
| Flavor | proper amount | proper amount | proper amount | proper amount | proper amount | proper amount |
| Purified water | bal. | bal. | bal. | bal. | bal. | bal. |
| Improving effect on rough skin | C | C | C | C | C | D |
| Stickiness | B | B | A | A | A | A |

As proved above, little improving effect on the skin is exerted by any of the combination of tranexamic acid and ginseng extract (Comparative Example 1), tranexamic acid alone (Comparative Example 2), the combination of disodium adenosine triphophate and ginseng extract (Comparative Example 3), disodium adenosine triphophate alone (Comparative Example 4) and ginseng extract alone (Comparative Example 5). To the contrary, the combination of disodium adenosine triphophate and tranexamic acid (Example 5) exhibits an excellent improving effect on the skin. In particular, the combinations of disodium adenosine triphophate, tranexamic acid, and ginseng extract (Examples 1 to 4) produce very powerful improving effects on skin roughness even with the amount of each component being reduced to a tenth to a hundredth.

3) Practical Test Using Replica Method:

A replica of the surface condition of the facial skin of a healthy woman was taken using a silicon resin and observed under a microscope of 17 magnifications. The skin roughness was graded from the conditions of dermatoglyphs and the peeling conditions of the corneum based on the following standards. Those women whose skin was graded 1 or 2 were divided in 6 groups each consisting of 10 women. The lotion of Example 2 or 5 was applied to the right half of the face while the lotion of Comparative Examples 1 to 6 was applied to the left half each twice a day. Two weeks later, a replica was again taken, and the skin conditions were observed and graded in the same manner as above. The results obtained are shown in Table 3 below.

Grading Standards:
1. Disappearance of dermatoglyphs and ridges of skin surface and peeling of the corneum over a wide area were observed.
2. Dermatoglyphs and ridges of skin surface became vague, and peeling of the corneum was observed.
3. Dermatoglyphs and ridges of skin surface were discerned but flat.
4. Dermatoglyphs and ridges of skin surface were clear.
5. Dermatoglyphs and ridges of skin surface were clear and regular.

Rating Standards:
A. Average score not lower than 4
B. Average score not lower than 3 and lower than 4
C. Average score not lower than 2 and lower than 3
D. Average score lower than 2

TABLE 3

| | Example No. | | Comparative Example No. | | | | |
|---|---|---|---|---|---|---|---|
| | 2 | 5 | 1 | 2 | 3 | 4 | 5 | 6 |
| Grade | A | B | C | C | C | C | C | D |

It can be seen from Table 3 that the preparations according to the present invention exhibit excellent improving effects on skin roughness.

In the following Examples 6 to 13 preparations for external application were prepared. All of the preparations exhibited effects of preventing skin roughness and improving the skin conditions without causing papules, comedos, pustules or erythema.

EXAMPLE 6

| Facial Pack | |
|---|---|
| Polyvinyl alcohol | 15.0 wt % |
| Tranexamic acid | 0.01 |
| Disodium adenosine triphophate | 0.0005 |
| Ginseng extract | 10.0 |
| Methyl cellulose | 0.5 |
| Propylene glycol | 5.0 |
| Sodium keratosulfate | 0.005 |
| Enzymolysis product of egg white | 0.8 |
| Ethanol | 8.0 |
| Ethyl p-hydroxybenzoate | 0.1 |
| Perfume | proper amount |
| Purified water | balance |

EXAMPLE 7

| Moistening Cream | |
|---|---|
| Stearic acid | 2.0 wt % |
| Stearyl alcohol | 3.0 |
| Reduced lanolin | 2.0 |
| Octyldodecanol | 6.0 |
| Maltitol hydroxylauryl ether | 3.0 |
| Glycerol monostearate | 2.0 |
| Antiseptic | proper amount |
| Perfume | proper amount |
| Propylene glycol | 10.0 |
| Glycerin | 3.0 |
| Hyaluronic acid | 2.0 |
| Enzymolysis product of egg white | 0.01 |
| Tranexamic acid | 5.0 |
| Disodium adenosine triphophate | 5.0 |
| Ginseng extract | 0.005 |
| Purified water | balance |

EXAMPLE 8

| Milky Lotion | |
|---|---|
| Stearic acid | 1.0 wt % |
| Cetanol | 1.5 |
| Vaseline | 3.0 |
| Lanolin alcohol | 2.0 |
| Liquid paraffin | 8.0 |
| Squalane | 5.0 |
| Jojoba oil | 1.0 |
| V-E acetate | 0.5 |
| 2-Ethylhexyl p-methoxycinnate | 0.5 |

-continued

| Milky Lotion | |
|---|---|
| POE (20) behenyl ether | 1.5 |
| POE (10) monooleate | 1.0 |
| Triethanolamine | 1.0 |
| 1,3-Butylene glycol | 10.0 |
| Dipropylene glycol | 8.0 |
| Chondroitin sulfate | 0.05 |
| Tranexamic acid | 5.0 |
| Disodium adenosine triphophate | 0.01 |
| Ginseng extract | 5.0 |
| Purified water | balance |

EXAMPLE 9

| Milkyl Lotion | |
|---|---|
| Stearic acid | 1.0 wt % |
| Behenic acid | 1.0 |
| Behenyl alcohol | 2.0 |
| Dimethylpolysiloxane | 3.0 |
| Macademia nut oil | 1.0 |
| Vaseline | 3.0 |
| Stearyl glycyrrhetinate | 0.1 |
| Glycerol tri(2-ethylhexanoate) | 2.0 |
| Evening primrose oil | 0.1 |
| Vitamin E | 0.1 |
| Placenta extract | 0.1 |
| Magnesium ascorbic acid phosphate | 0.1 |
| Tranexamic acid | 0.1 |
| Disodium adenosine triphophate | 0.001 |
| Ginseng extract | 0.01 |
| Trisodium edetate | 0.1 |
| Carboxyvinyl polymer | 0.2 |
| Propylene glycol | 5.0 |
| Dipropylene glycol | 10.0 |
| Sodium hyaluronate | 0.2 |
| Potassium hydroxide | 0.1 |
| Antiseptic | proper amount |
| Perfume | proper amount |
| Purified water | balance |

EXAMPLE 10

| Clear Lotion | |
|---|---|
| Sorbitol | 2.0 wt % |
| Dipropylene glycol | 5.0 |
| Sodium chondroitin sulfate | 1.0 |
| Sodium metaphosphate | 0.1 |
| Dipotassium glycyrrhizinate | 0.1 |
| Tranexamic acid | 3.0 |
| Disodium adenosine triphophate | 0.5 |
| Ginseng extract | 7.0 |
| Ethanol | 10.0 |
| POE (50) hardened castor oil | 0.5 |
| Antiseptic | proper amount |
| Perfume | proper amount |
| Purified water | balance |

EXAMPLE 11

| Lip Treatment | |
|---|---|
| Candellila wax | 9.0 wt % |
| Solid paraffin | 8.0 |
| Molasses | 5.0 |
| Carnauba wax | 5.0 |
| Lanolin | 10.0 |

-continued

| Lip Treatment | |
|---|---|
| Castor oil | balance |
| Chitin | 0.07 |
| Tranexamic acid | 0.01 |
| Disodium adenosine triphophate | 0.0001 |
| Ginseng extract | 0.005 |
| Isopropyl myristate | 10.0 |
| Deionized water | 0.5 |
| Perfume | proper amount |
| Antioxidant | proper amount |

EXAMPLE 12

| Aqueous Gel | |
|---|---|
| 1,3-Butylene glycol | 5.0 wt % |
| Glycerin | 20.0 |
| Maltitol | 3.0 |
| Ethyl cellulose | 0.3 |
| Carboxyvinyl polymer | 0.5 |
| Tranexamic acid | 1.0 |
| Ginseng extract | 0.05 |
| Disodium adenosine triphophate | 0.005 |
| Potassium hydroxide | 0.15 |
| POE (50) hardened castor oil | 1.0 |
| Nylon powder | 2.0 |
| Squalane | 3.0 |
| Antiseptic | proper amount |
| Perfume | proper amount |
| Colorant | proper amount |
| Trisodium edetate | 0.01 |

EXAMPLE 13

| Essence | |
|---|---|
| Sorbitol | 2.0 wt % |
| Dipropylene glycol | 5.0 |
| Sodium chondroitin sulfate | 1.0 |
| Sodium metaphosphate | 0.1 |
| Dipotassium glycyrrhizinate | 0.1 |
| Tranexamic acid | 3.0 |
| Disodium adenosine triphophate | 0.5 |
| Ginseng extract | 7.0 |
| Ethanol | 10.0 |
| POE (50) hardened castor oil | 0.5 |
| Glycerin | 10.0 |
| Carboxyvinyl polymer | 0.5 |
| Potassium hydroxide | 0.22 |
| Antiseptic | proper amount |
| Perfume | proper amount |
| Purified water | balance |

As has been fully described, the preparations according to the present invention have excellent effect of preventing skin roughening and improving the skin conditions and high safety.

While the invention has been described in detail and with reference to specific examples thereof, it will be apparent to one skilled in the art that various changes and modifications can be made therein without departing from the spirit and scope thereof.

What is claimed is:

1. A preparation for external application to the skin which comprises 0.0005 to 3.0% by weight disodium adenosine triphosphate, 0.01 to 3.0% by weight tranexamic acid, and 0.005 to 10.0% by weight ginseng extract.

2. The preparation for external application to the skin as claimed in claim 1, which is for amelioration of skin roughening.

3. A method for amelioration of skin roughening which comprises application to human skin of an effective amount of a preparation as claimed in claim 1 and pharmaceutically or cosmetically acceptable carriers and diluents.

4. A method of manufacturing a medicament or cosmetic for amelioration of skin roughening, said method comprising combining 0.0005 to 3.0% by weight disodium adenosine triphosphate, 0.01 to 3.0% by weight tranexamic acid and 0.005 to 10.0% by weight ginseng extract to obtain said medicament or cosmetic.

* * * * *